(12) United States Patent
Seo et al.

(10) Patent No.: US 12,349,315 B2
(45) Date of Patent: Jul. 1, 2025

(54) BEAUTY CARE APPARATUS

(71) Applicant: ASTERASYS CO., LTD., Seoul (KR)

(72) Inventors: Eun Taek Seo, Seoul (KR); Jong Seok Kim, Seoul (KR)

(73) Assignee: ASTERASYS CO., LTD., Seoul (KR)

( * ) Notice: Subject to any disclaimer, the term of this patent is extended or adjusted under 35 U.S.C. 154(b) by 0 days.

(21) Appl. No.: 18/473,268

(22) PCT Filed: Oct. 7, 2021

(86) PCT No.: PCT/KR2021/013782
§ 371 (c)(1),
(2) Date: Sep. 24, 2023

(87) PCT Pub. No.: WO2023/033230
PCT Pub. Date: Mar. 9, 2023

(65) Prior Publication Data
US 2024/0431076 A1  Dec. 26, 2024

(30) Foreign Application Priority Data

Sep. 2, 2021  (KR) .......................... 10-2021-0117100

(51) Int. Cl.
*A61N 7/00* (2006.01)
*H05K 7/20* (2006.01)

(52) U.S. Cl.
CPC ............ *H05K 7/2039* (2013.01); *A61N 7/00* (2013.01); *H05K 7/20272* (2013.01); *A61N 2007/0034* (2013.01)

(58) Field of Classification Search
CPC .... H05K 7/2039; H05K 7/20272; A61N 7/00; A61N 2007/0034; A61F 2007/0075; A61F 2007/0087; A61F 7/00
See application file for complete search history.

(56) References Cited

U.S. PATENT DOCUMENTS

| | | | |
|---|---|---|---|
| 2008/0077211 A1* | 3/2008 | Levinson | A61F 7/10 607/108 |
| 2011/0077557 A1* | 3/2011 | Wing | A61B 8/546 601/2 |

FOREIGN PATENT DOCUMENTS

| | | | |
|---|---|---|---|
| KR | 10-2014-0013643 A | 2/2014 | |
| KR | 10-1394214 B1 | 5/2014 | |
| KR | 10-2014-0144420 A | 12/2014 | |
| KR | 10-1641309 B1 | 7/2016 | |
| KR | 10-1648837 B1 | 8/2016 | |
| KR | 10-2019-0023842 A | 3/2019 | |
| KR | 10-2019-0063723 A | 6/2019 | |
| KR | 10-2165047 B1 | 10/2020 | |

* cited by examiner

*Primary Examiner* — Mark D Remaly
(74) *Attorney, Agent, or Firm* — AJU IP Global PLLC

(57) ABSTRACT

Disclosed is a beauty care apparatus, the beauty care apparatus of the present disclosure includes a housing part configured to accommodate a medium therein and formed of a thermally conductive material; a holder part disposed inside the housing part; an ultrasonic wave generator configured to be coupled to the holder part and generate ultrasonic waves; and a cooler installed in the housing part to cool the housing part.

5 Claims, 10 Drawing Sheets

FIG. 10

BEAUTY CARE APPARATUS

TECHNICAL FIELD

The present disclosure relates to a beauty care apparatus, and more particularly, to a beauty care apparatus preventing overheating of an ultrasonic wave generator and maintaining a skin contact part at a low temperature to reduce pain.

BACKGROUND ART

Generally, numerous skin care devices that prevent skin aging by massaging the face have been proposed. Beauty devices are used for skin care, physical therapy, obesity management, and the like. Beauty devices irradiate the skin with ultrasonic waves to increase skin elasticity and lift the skin. Also, beauty devices are also used to make ultrasonic waves reach the subcutaneous fat layer and reduce the subcutaneous fat.

However, in the conventional beauty device, as an ultrasonic wave generator 160 inside the beauty device generates heat, a housing is heated to a high temperature, and thus the use time of the beauty device is limited. Also, when a skin contact part of the housing is heated, the skin contact part may heat the skin and increase pain. Therefore, there is a need for improvement.

The related art of the present disclosure is disclosed in Korean Patent Application Publication No. 2014-0013643 (Date of Publication: Feb. 5, 2014, Title of Disclosure: skin beauty device).

DISCLOSURE

Technical Problem

The present disclosure is directed to providing a beauty care apparatus preventing overheating of an ultrasonic wave generator and maintaining a skin contact part at a low temperature to reduce pain.

Technical Solution

The present disclosure provides a beauty care apparatus including: a housing part configured to accommodate a medium therein and formed of a thermally conductive material; a holder part disposed inside the housing part; an ultrasonic wave generator configured to be coupled to the holder part and generate ultrasonic waves; and a cooler installed in the housing part to cool the housing part.

The housing part may include: a housing body part configured to accommodate the holder part; a housing cover part configured to be coupled to the housing body part and configured to be irradiated with ultrasonic waves generated from the ultrasonic wave generator; and a heat conductor connected to the housing body part and the cooler to cool the housing body part.

The housing body part, the housing cover part, and the heat conductor may be formed of a thermally conductive material.

The heat conductor may be provided as a plurality of heat conductors installed to surround the housing body part.

The heat conductor may include: a contact panel part configured to come in contact with the cooler; and a heat conduction panel part configured to extend from the contact panel part to come in contact with an outer side surface of the housing body part.

A flat part may be formed on the outer side surface of the housing body part, and a flat heat conduction surface part may be formed on the heat conduction panel part to come in contact with the flat part.

The cooler may be one or more Peltier elements having a cooling surface part seated on the contact panel part.

The beauty care apparatus may further include a heat dissipation unit configured to come in contact with a heat generation surface part of the Peltier elements so that heat is dissipated from the heat generation surface part.

The heat dissipation unit may include: a heat dissipation block configured to be seated on the heat generation surface part and have a heat dissipation space part formed therein; a supply tube part connected to the heat dissipation block to supply a heat dissipation medium to the heat dissipation space part; and a discharge tube part connected to the heat dissipation block to discharge the heat dissipation medium from the heat dissipation space part.

The cooler may be a plurality of Peltier elements disposed in a peripheral direction of the housing part at one side of the housing part.

The beauty care apparatus may further include a heat dissipation unit configured to come in contact with a plurality of heat generation surface parts so that heat is dissipated from the plurality of heat generation surface parts.

The heat dissipation unit may include: a heat dissipation block configured to come in contact with the plurality of heat generation surface parts and have a heat dissipation space part formed therein; a supply tube part connected to the heat dissipation block to supply a heat dissipation medium to the heat dissipation space part; and a discharge tube part connected to the heat dissipation block to discharge the heat dissipation medium from the heat dissipation space part.

The plurality of Peltier elements may be installed in an upright state on an outer side surface of the heat dissipation block.

Advantageous Effects

According to the present disclosure, since a cooler cools a housing part, when an ultrasonic wave generator irradiates ultrasonic waves in a state in which a contact part of the housing part is in contact with the skin, coldness of the housing part can prevent overheating of the skin. Therefore, as the skin is cooled, pain caused by heat can be remarkably reduced.

Also, according to the present disclosure, since the cooler cools the ultrasonic wave generator, damage to or deformation of the housing part caused by heat generated from the ultrasonic wave generator can be prevented.

In addition, according to the present disclosure, since the cooler cools the ultrasonic wave generator, overheating of the ultrasonic wave generator can be prevented, and the use time of the beauty care apparatus can be significantly increased.

MODES OF THE INVENTION

Hereinafter, embodiments of a beauty care apparatus according to the present disclosure will be described with reference to the accompanying drawings. In describing the beauty care apparatus, thicknesses of lines or sizes of elements illustrated in the drawings may be exaggerated for clarity and convenience of description. Also, terms used below are terms defined in consideration of functions in the present disclosure and may vary according to an intention or customary practice of a user or an operator. Therefore, the terms should be defined based on the content throughout the specification.

Figure 1:
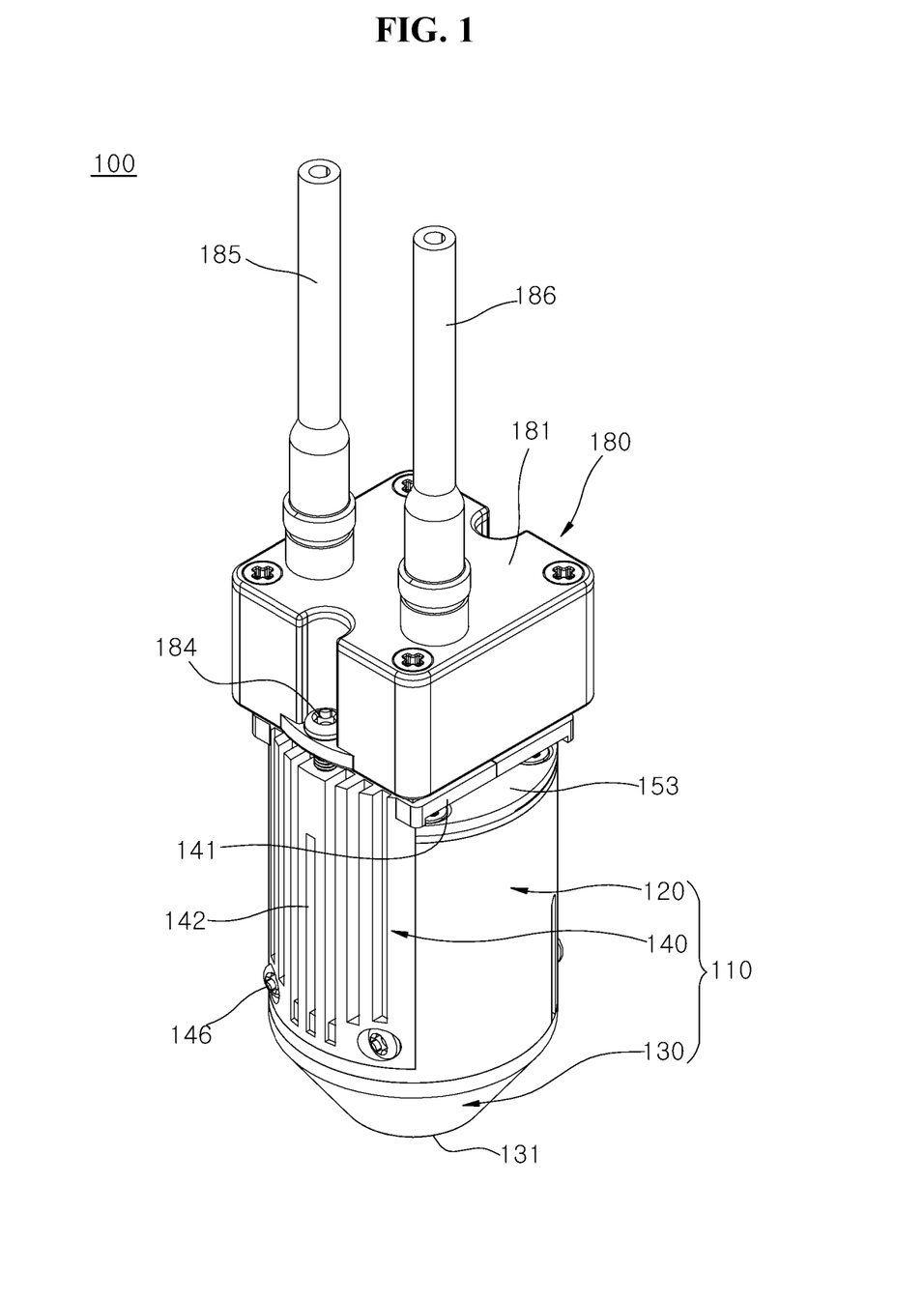
FIG. 1 is a perspective view illustrating a beauty care apparatus according to a first embodiment of the present disclosure.
Figure 2:
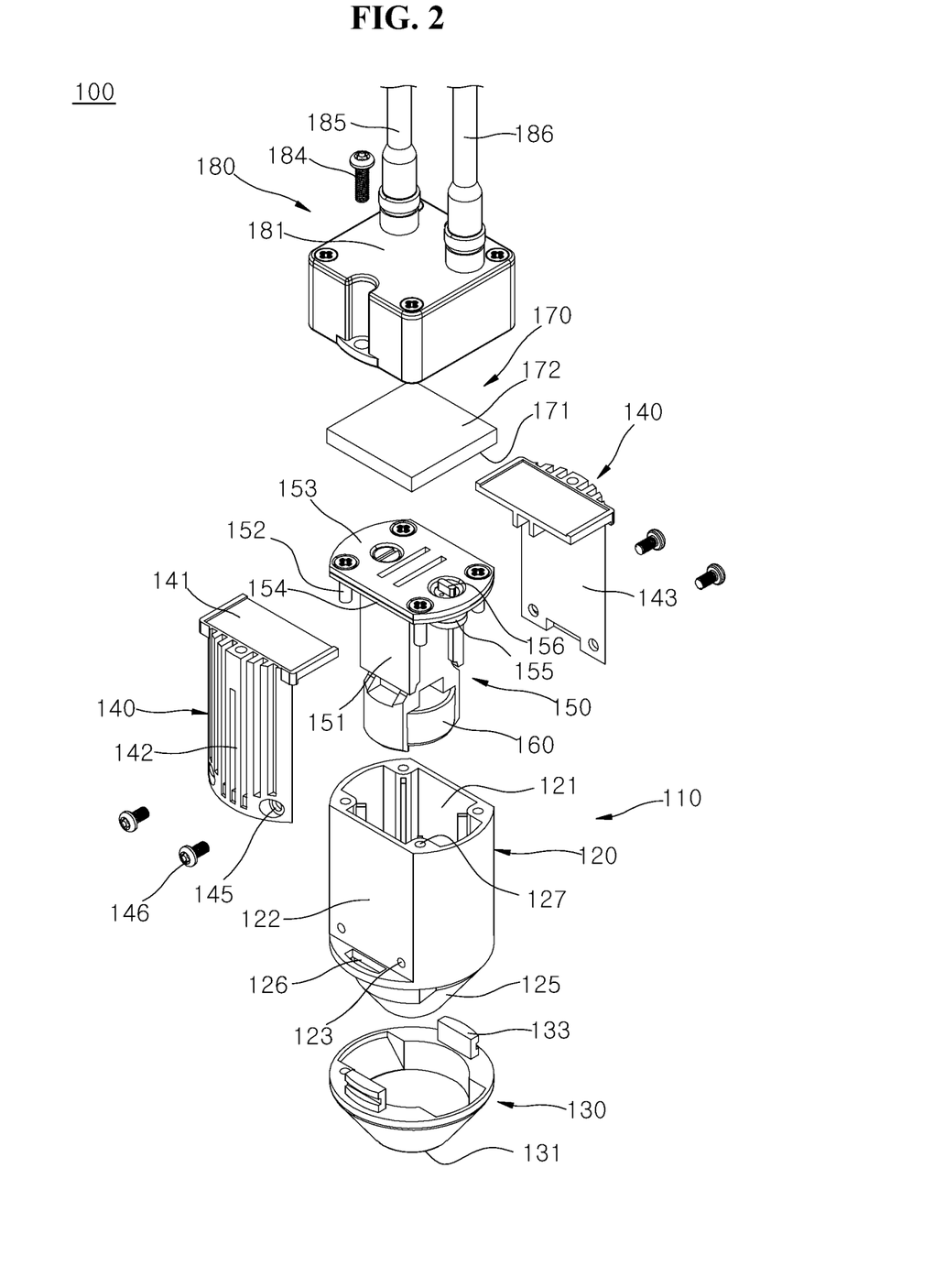
FIGS. 2 and 3 are exploded perspective views illustrating the beauty care apparatus according to the first embodiment of the present disclosure.
Figure 3:
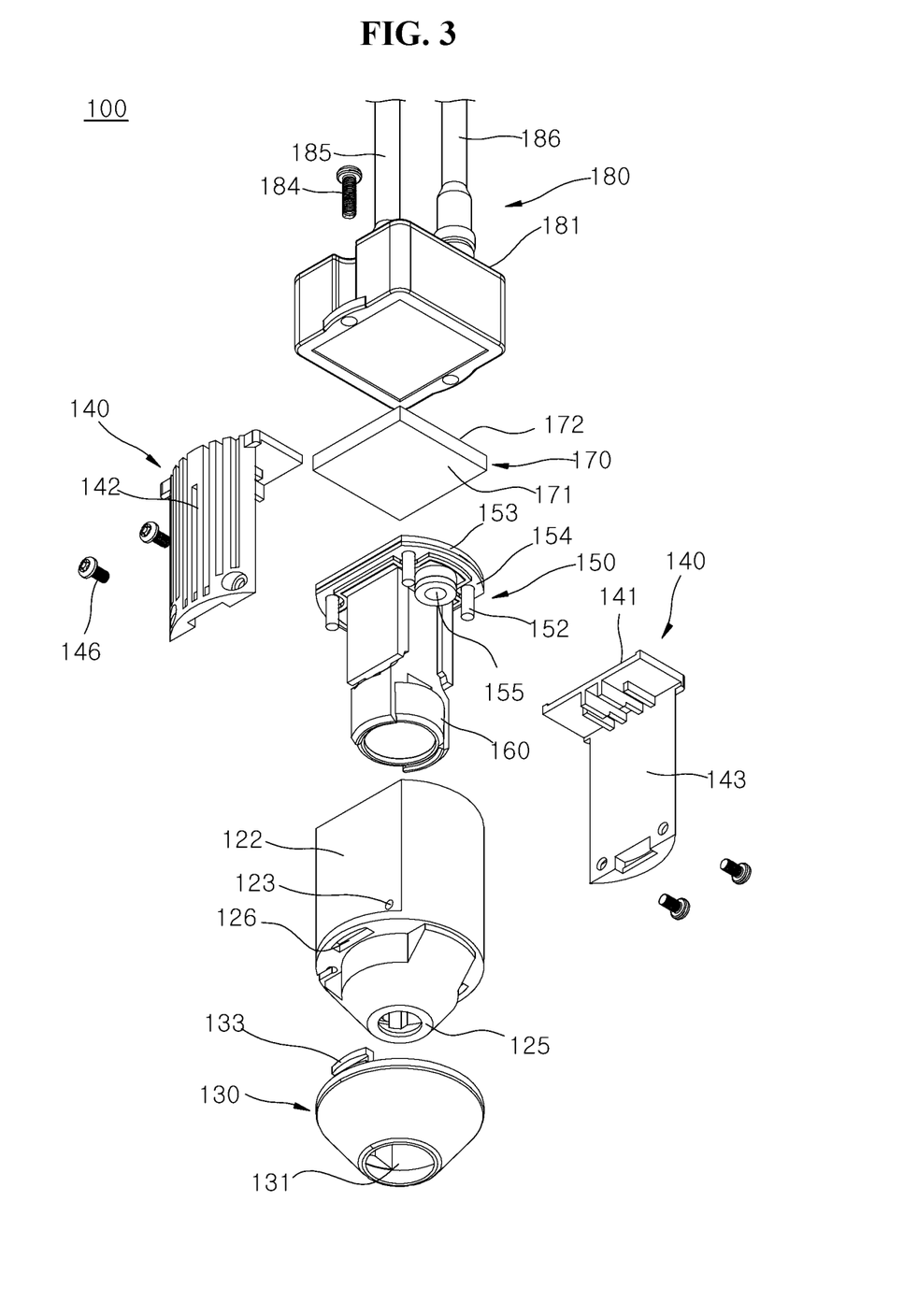
Figure 4:
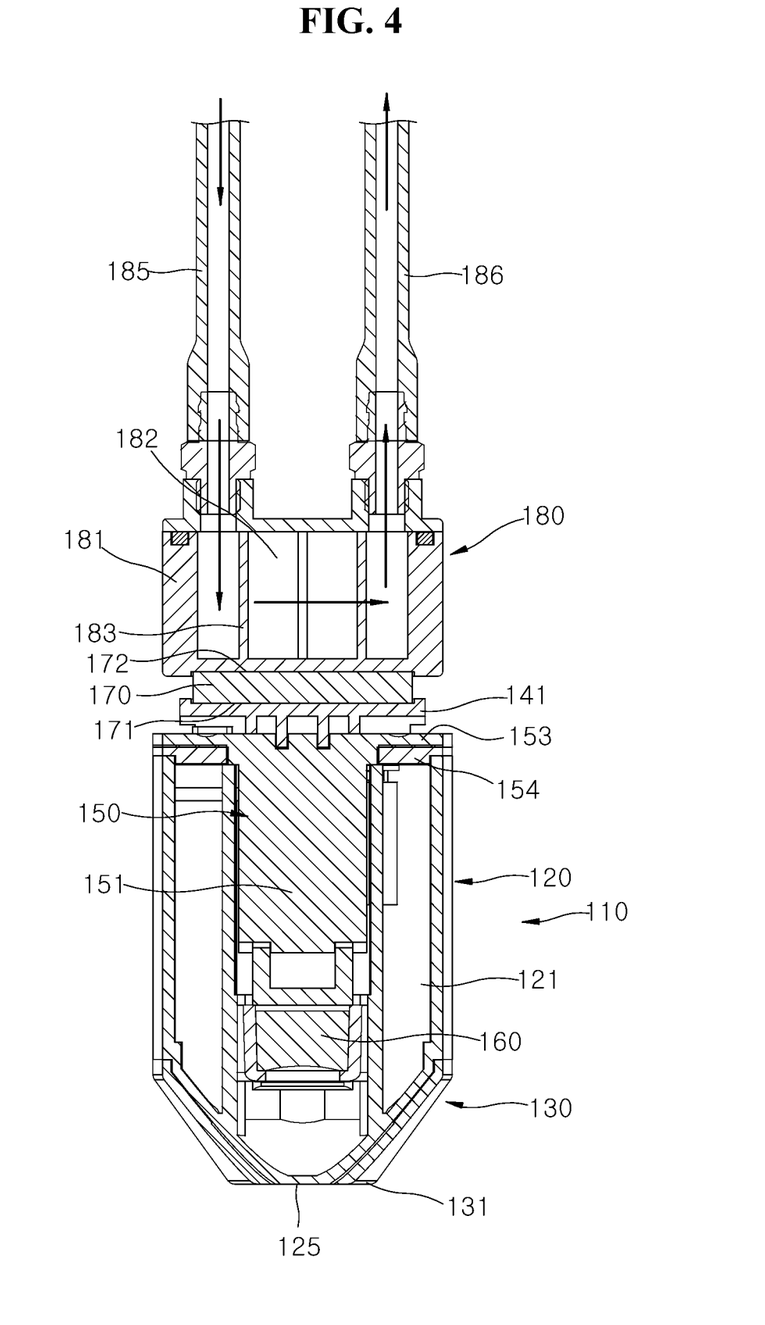
FIGS. 4 and 5 are cross-sectional views illustrating the beauty care apparatus according to the first embodiment of the present disclosure.
Figure 5:
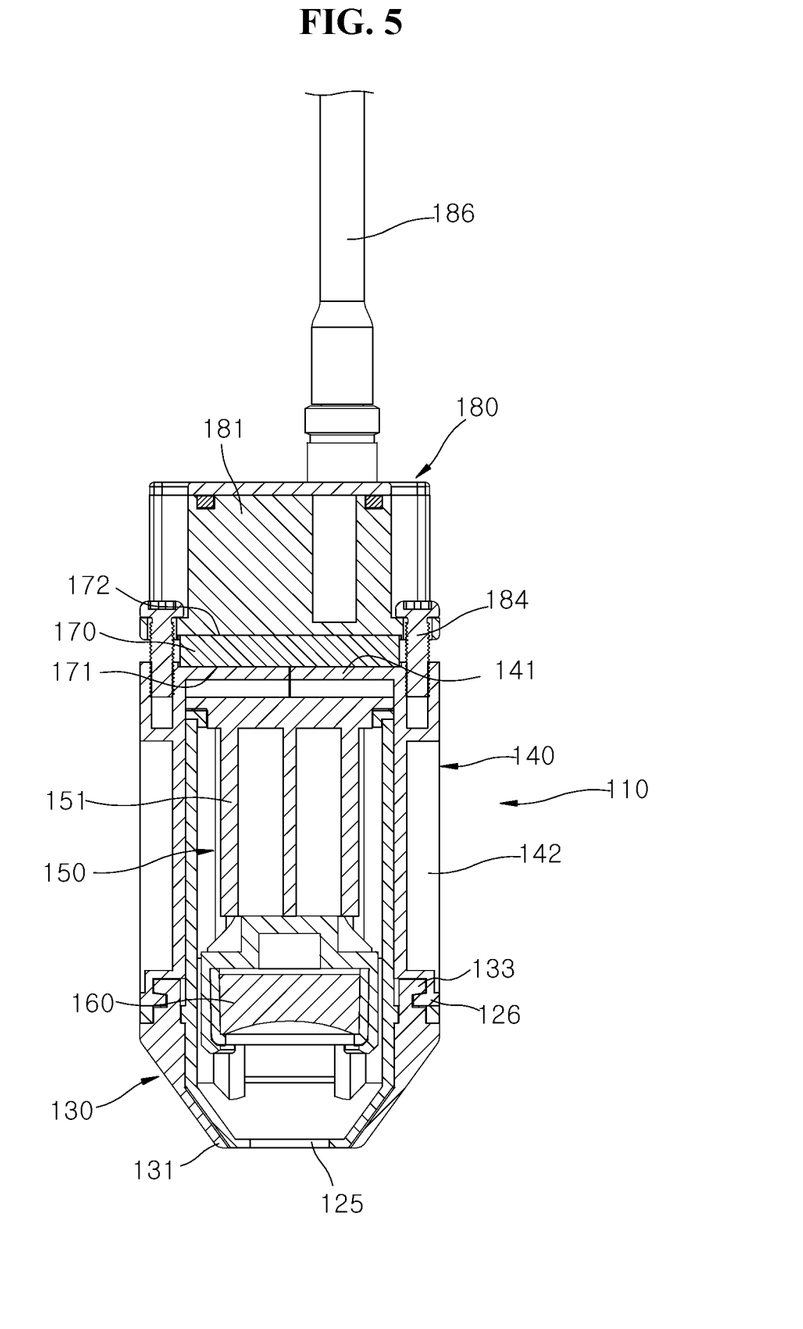

FIG. 1 is a perspective view illustrating a beauty care apparatus according to a first embodiment of the present disclosure, FIGS. 2 and 3 are exploded perspective views illustrating the beauty care apparatus according to the first embodiment of the present disclosure, and FIGS. 4 and 5 are cross-sectional views illustrating the beauty care apparatus according to the first embodiment of the present disclosure.

Referring to FIGS. 1 to 5, a beauty care apparatus 100 according to the first embodiment of the present disclosure includes a housing part 110, a holder part 150, an ultrasonic wave generator 160, and a cooler 170.

The housing part 110 accommodates a medium therein and is formed of a thermally conductive material. An accommodation space part 121 is formed inside the housing part 110 to accommodate the medium. Various types of media, such as deionized (DI) water through which ultrasonic waves generated from the ultrasonic wave generator 160 pass, may be applied as the medium. Also, the housing part 110 is formed of a material with excellent thermal conductivity, such as an aluminum material.

The holder part 150 is disposed inside the housing part 110. The holder part 150 closes an opening of the housing part 110 to prevent leakage of the medium to the outside. The holder part 150 is installed to adjust the height of the ultrasonic wave generator 160.

The ultrasonic wave generator 160 is coupled to the holder part 150 and generates ultrasonic waves. A transducer is proposed as the ultrasonic wave generator 160. The transducer generates high-intensity focused ultrasound (HIFU). As power is applied to the ultrasonic wave generator 160, the ultrasonic wave generator 160 generates ultrasonic waves, focuses the ultrasonic waves, and then irradiates the skin with the ultrasonic waves. The ultrasonic wave generator 160 is cooled by the medium when in contact with the medium, and thus the efficiency of the ultrasonic wave generator 160 can be significantly improved, and the use time of the beauty care apparatus 100 can be significantly increased.

The cooler 170 is installed in the housing part 110 to cool the housing part 110. Since the cooler 170 cools the housing part 110, when the ultrasonic wave generator 160 irradiates ultrasonic waves in a state in which a contact part 131 of the housing part 110 is in contact with the skin, coldness of the housing part 110 can prevent overheating of the skin.

Therefore, as the skin is cooled, pain caused by heat may be remarkably reduced. Further, damage to or deformation of the housing part 110 caused by heat generated from the ultrasonic wave generator 160 can be prevented. Various types of cooling elements, such as a cooling element circulating a cooling medium to generate cold air or supplying electricity to generate cold air, may be applied as the cooler 170.

The housing part 110 includes a housing body part 120, a housing cover part 130, and a heat conductor 140.

The holder part 150 is accommodated in the housing body part 120. A plurality of fastening hole parts 123 are formed in the housing body part 120. A sealing film part 125 is installed at one side of the housing body part 120 to prevent leakage of the medium and allow passage of ultrasonic waves. The sealing film part 125 may be laminated on a lower side of the housing body part 120.

The housing cover part 130 is coupled to the housing body part 120 and is irradiated with ultrasonic waves generated from the ultrasonic wave generator 160. The contact part 131 is formed at one side of the housing cover part 130 to come in contact with the skin and irradiate the skin with the ultrasonic waves. The contact part 131 may be formed in an annular shape. Also, a plurality of hook parts 133 are formed on the housing cover part 130, and a restrainer 126 is formed on the lower side of the housing body part 120 so that the hook part 133 is caught in and restrained by the restrainer 126.

The heat conductor 140 is connected to the housing body part 120 and the cooler 170 to cool the housing body part 120. A plurality of through-hole parts 145 are formed in the heat conductor 140, and the plurality of fastening hole parts 123 are formed in the housing body part 120 to correspond to the through-hole parts 145. As a fastening member 146 passes through the through-hole part 145 and is fastened to the fastening hole part 123, the heat conductor 140 is coupled to the housing body part 120. Since the heat conductor 140 is connected to the housing body part 120 and the cooler 170, cooling energy of the cooler 170 is conducted to the housing body part 120 and the housing cover part 130 through the heat conductor 140. As the housing body part 120 is cooled by the heat conductor 140, the medium accommodated in the housing body part 120 is cooled. Also, since the contact part 131 of the housing cover part 130 is cooled as the housing body part 120 conducts the cooling energy to the housing cover part 130, as the skin is cooled by the housing cover part 130, pain caused by heat can be remarkably reduced.

The holder part 150 includes a holder body part 151 in which the accommodation space part 121 is formed, a lid part 153 configured to cover an opening of the holder body part 151, and a sealing part 154 interposed between the lid part 153 and the holder body part 151 to seal a gap between the lid part 153 and the holder body part 151. The lid part 153 may be formed in a plate shape to cover the accommodation space part 121, and the sealing part 154 may be formed in the shape of a quadrangular frame along the periphery of the lid part 153. An injection part 155 is formed in the lid part 153 to inject a medium into the accommodation space part 121, and the injection part 155 is closed by a stopper part 156. A plurality of holder fastening parts 152 are formed on the lid part 153, and the plurality of holder fastening parts 152 are each fastened to a groove part 127 of the housing body part 120. Here, the sealing part 154 seals a gap between the housing body part 120 and the lid part 153.

The housing body part 120, the housing cover part 130, and the heat conductor 140 are formed of a thermally conductive material. For example, the housing body part 120, the housing cover part 130, and the heat conductor 140 include an aluminum material. Accordingly, cold air generated from the cooler 170 may be conducted to the housing body part 120 and the housing cover part 130 through the heat conductor 140 to cool the ultrasonic wave generator 160, and the skin may be cooled for skin treatment or skin care. Also, since the cold air of the cooler 170 cools the ultrasonic wave generator 160 through a medium, overheating of the ultrasonic wave generator 160 can be prevented, and the operation time of the ultrasonic wave generator 160 can be significantly increased. Therefore, the use time of the beauty care apparatus 100 can be significantly increased. Further, damage to or deformation of the housing part 110 caused by heat generated from the ultrasonic wave generator 160 can be prevented.

A plurality of heat conductors 140 is installed to surround the housing body part 120. Since the plurality of heat conductors 140 cool the housing body part 120, the housing body part 120 may be thoroughly cooled. Therefore, various heat transfer paths may be configured by the heat conductors 140. The number of installed heat conductors 140 may be appropriately determined in consideration of the capacity of the ultrasonic wave generator 160 or the size of the beauty care apparatus 100.

The heat conductor 140 includes a contact panel part 141 configured to come in contact with the cooler 170 and a heat conduction panel part 142 configured to extend from the contact panel part 141 to come in contact with an outer side surface of the housing body part 120. The contact panel part 141 is horizontally disposed to come in close contact with a cooling surface part 171 of the cooler 170, and the heat conduction panel part 142 is vertically disposed in the longitudinal direction of the housing body part 120. The contact panel part 141 and the heat conduction panel part 142 are installed to form the right angle or an angle close to the right angle. The heat conduction panel part 142 may be formed to have a length that is almost the same as the length of the housing body part 120.

A flat part 122 is formed on the outer side surface of the housing body part 120, and a flat heat conduction surface part 143 is formed on the heat conduction panel part 142 to come in contact with the flat part 122. Accordingly, a thermal contact area of the housing part 110 and the heat conduction panel part 142 may be increased. Also, a plurality of heat conduction fin parts (not illustrated) may be formed on the outer side surface of the housing body part 120, and heat conduction groove parts (127) may be formed in the heat conduction panel part 142 so that the heat conduction fin parts are fitted into the heat conduction groove parts. Forms of contact between the housing body part 120 and the heat conduction panel part 142 may vary.

The cooler 170 includes one or more Peltier elements having the cooling surface part 171 seated on the contact panel part 141. The one or more Peltier elements may be horizontally disposed so that the cooling surface part 171 is seated on the contact panel part 141. For example, a single large-sized Peltier element may be seated on the contact panel part 141, or a plurality of small-sized Peltier elements may be seated on the contact panel part 141. The number of Peltier elements may be appropriately determined in consideration of the capacity of the Peltier element, the capacity of the ultrasonic wave generator 160, the size of the beauty care apparatus 100, and the like.

The beauty care apparatus 100 further includes a heat dissipation unit 180 configured to come in contact with a heat generation surface part 172 of the Peltier elements so that heat is dissipated from the heat generation surface part 172. Since the heat dissipation unit 180 comes in contact with the heat generation surface part 172 of the Peltier elements, heat may be promptly dissipated from the heat generation surface part 172 of the Peltier elements. Therefore, the cooling efficiency of the Peltier elements can be further improved.

The heat dissipation unit 180 includes a heat dissipation block 181, a supply tube part 185, and a discharge tube part 186.

The heat dissipation block 181 is seated on the heat generation surface part 172 and has a heat dissipation space part 182 formed therein. The heat dissipation block 181 may be made of an aluminum material or the like with excellent thermal conductivity. A plurality of heat dissipation fins may be formed to protrude from the heat dissipation space part 182 to increase the heat exchange efficiency of a heat dissipation medium.

The supply tube part 185 is connected to the heat dissipation block 181 to supply a heat dissipation medium to the heat dissipation space part 182. The supply tube part 185 is connected to a side of the heat dissipation block 181 that is opposite to the housing part 110. The supply tube part 185 is connected to a cooling tank of the beauty care apparatus 100. The cooling tank may accommodate the heat dissipation medium and have a radiator or the like installed therein to cool the heat dissipation medium.

The discharge tube part 186 is connected to the heat dissipation block 181 to discharge the heat dissipation medium from the heat dissipation space part 182. The discharge tube part 186 is connected to the side of the heat dissipation block 181 that is opposite to the housing part 110. The discharge tube part 186 is connected to the cooling tank of the beauty care apparatus 100.

The supply tube part 185 supplies the heat dissipation medium to the heat dissipation block 181, and the heat dissipation medium heat-exchanged at the heat dissipation block 181 is discharged to the cooling tank through the discharge tube part 186. Therefore, as hot air of the heat generation surface part 172 of the Peltier element is released to the heat dissipation medium through the heat dissipation block 181, overheating of the Peltier element can be prevented.

Next, a beauty care apparatus according to a second embodiment of the present disclosure will be described.

Figure 6:
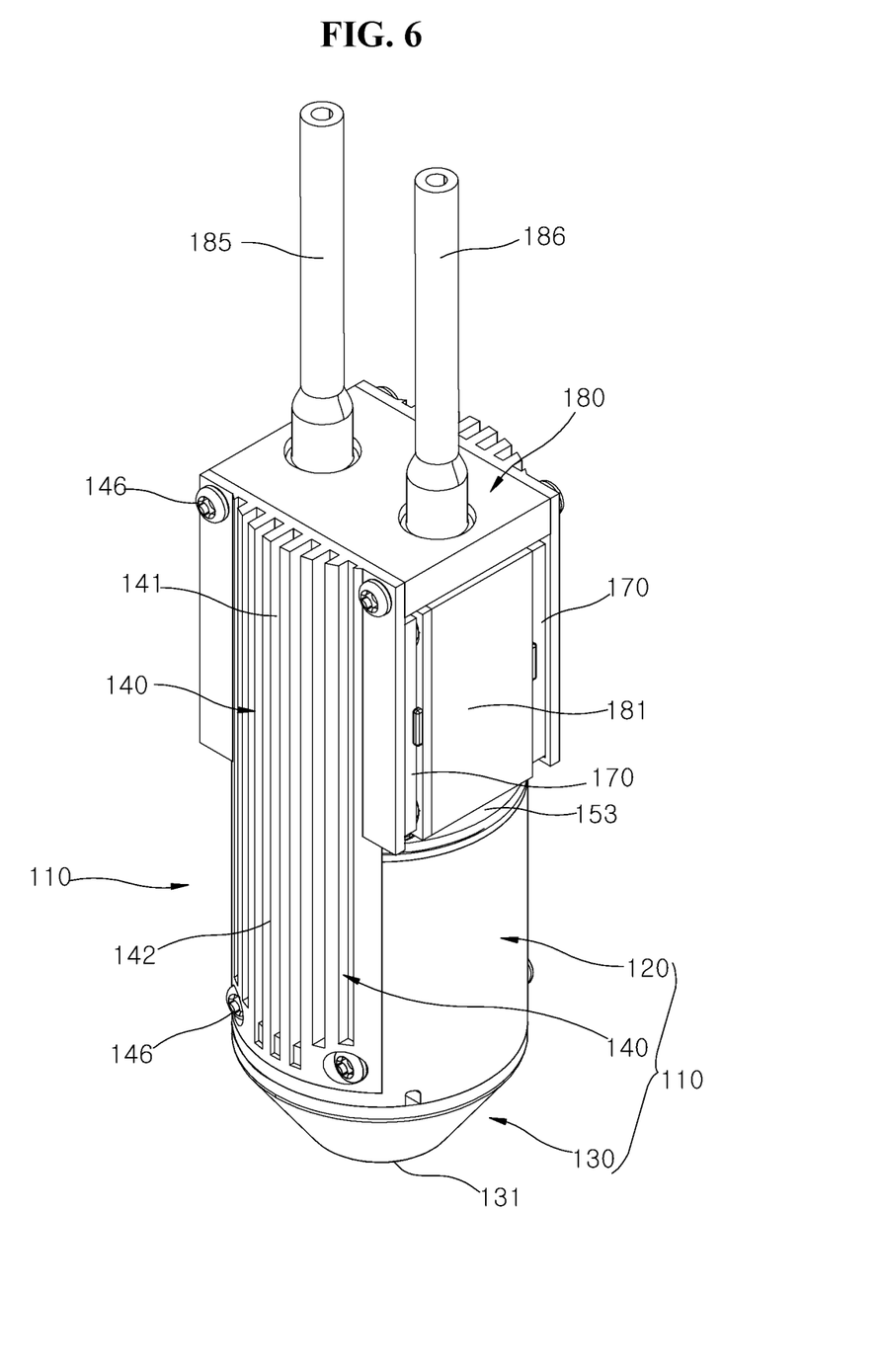
FIG. 6 is a perspective view illustrating a beauty care apparatus according to a second embodiment of the present disclosure.
Figure 7:
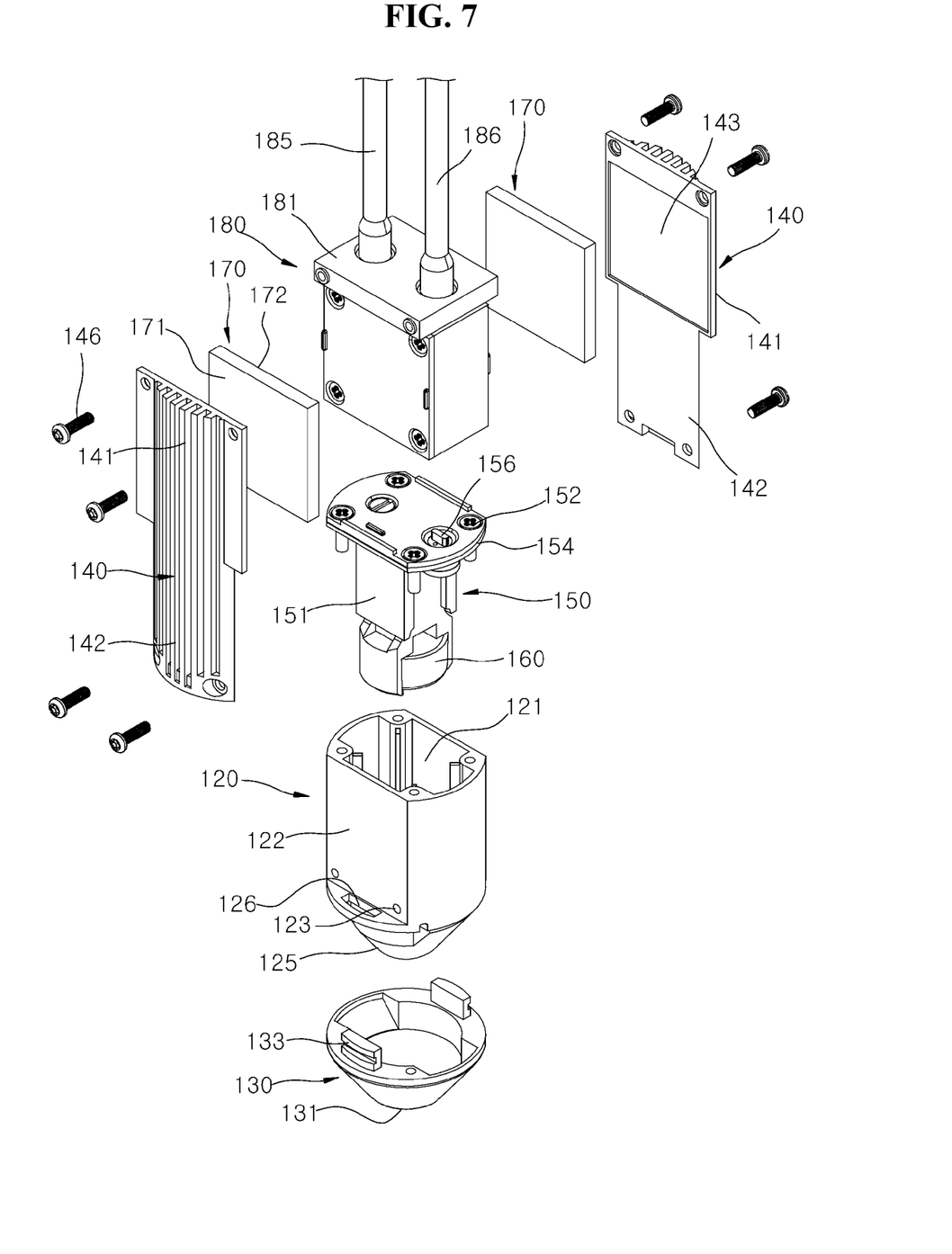
FIGS. 7 and 8 are exploded perspective views illustrating the beauty care apparatus according to the second embodiment of the present disclosure.
Figure 8:
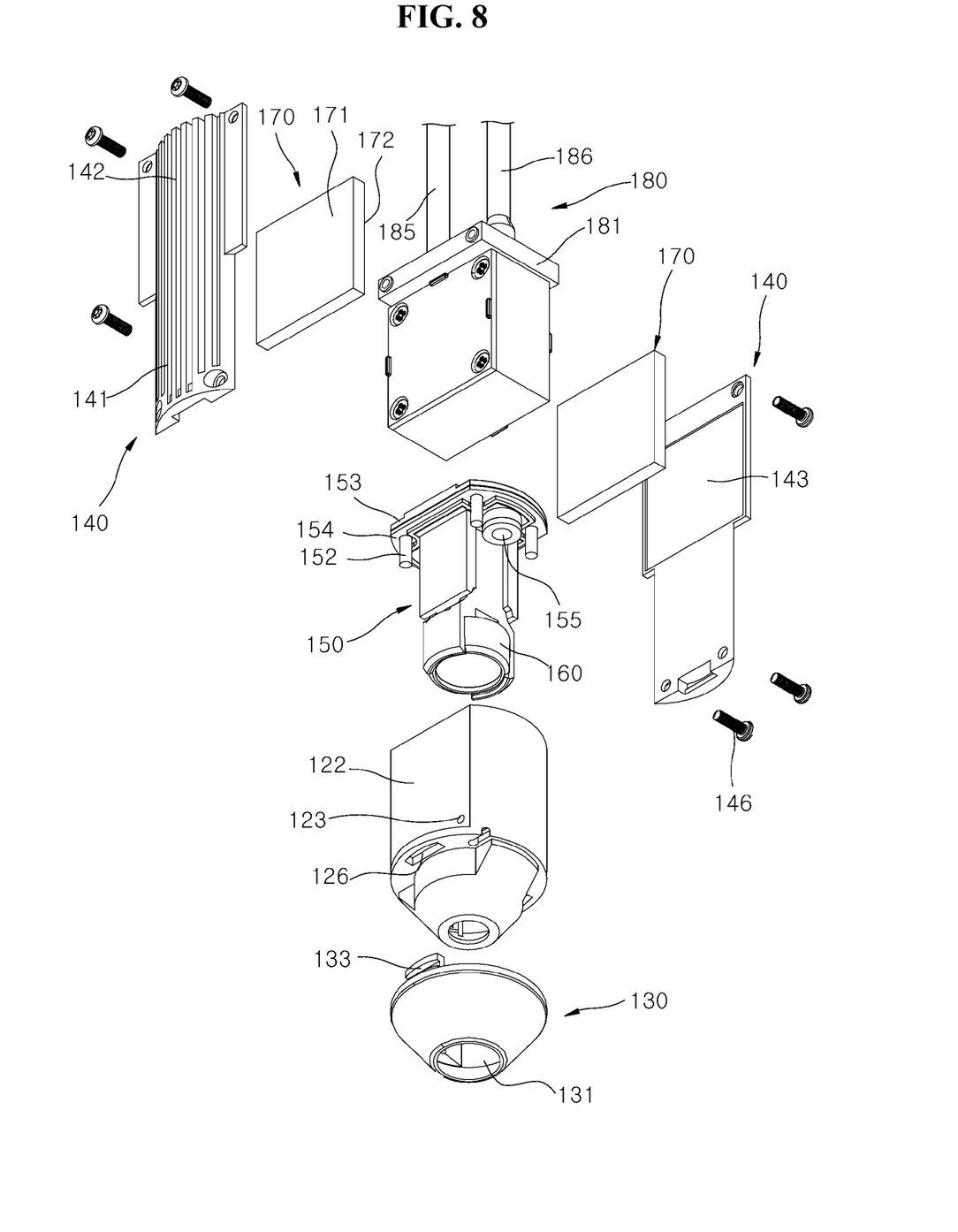
Figure 9:
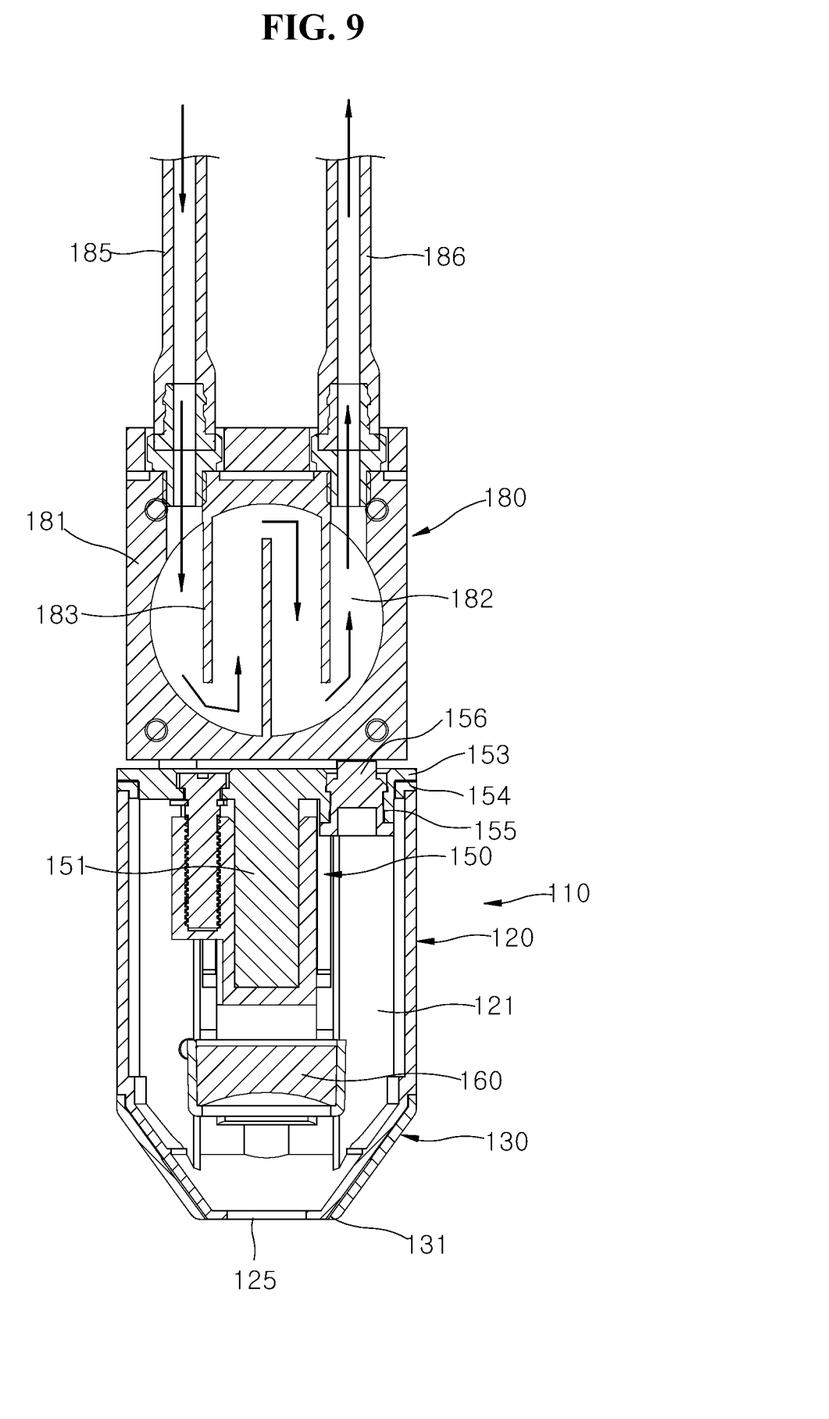
FIGS. 9 and 10 are cross-sectional views illustrating the beauty care apparatus according to the second embodiment of the present disclosure.
Figure 10:
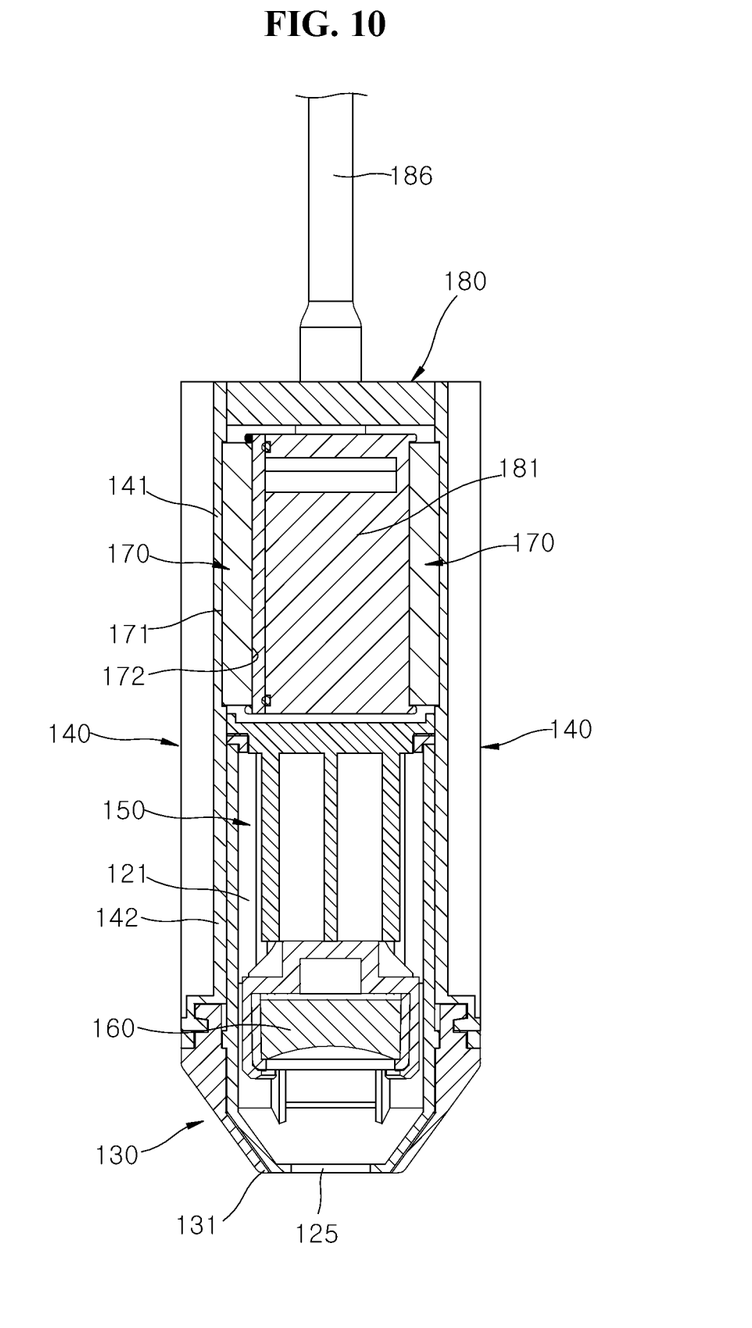

FIG. 6 is a perspective view illustrating the beauty care apparatus according to the second embodiment of the present disclosure, FIGS. 7 and 8 are exploded perspective views illustrating the beauty care apparatus according to the second embodiment of the present disclosure, and FIGS. 9 and 10 are cross-sectional views illustrating the beauty care apparatus according to the second embodiment of the present disclosure.

Referring to FIGS. 6 to 10, a beauty care apparatus 100 according to the second embodiment of the present disclosure includes a housing part 110, a holder part 150, an ultrasonic wave generator 160, and a cooler 170.

The housing part 110 accommodates a medium therein and is formed of a thermally conductive material. An accommodation space part 121 is formed inside the housing part 110 to accommodate the medium. Various types of media, such as deionized (DI) water through which ultrasonic waves generated from the ultrasonic wave generator 160 pass, may be applied as the medium. Also, the housing part 110 is formed of a material with excellent thermal conductivity, such as an aluminum material.

The holder part 150 is disposed inside the housing part 110. The holder part 150 closes an opening of the housing part 110 to prevent leakage of the medium to the outside. The holder part 150 is installed to adjust the height of the ultrasonic wave generator 160.

The ultrasonic wave generator 160 is coupled to the holder part 150 and generates ultrasonic waves. A transducer is proposed as the ultrasonic wave generator 160. The transducer generates HIFU. As power is applied to the ultrasonic wave generator 160, the ultrasonic wave generator 160 generates ultrasonic waves, focuses the ultrasonic waves, and then irradiates the skin with the ultrasonic waves. The ultrasonic wave generator 160 is cooled by the medium when in contact with the medium, and thus the efficiency of the ultrasonic wave generator 160 can be significantly improved.

The cooler 170 is installed in the housing part 110 to cool the housing part 110. Since the cooler 170 cools the housing part 110, when the ultrasonic wave generator 160 irradiates ultrasonic waves in a state in which a contact part 131 of the housing part 110 is in contact with the skin, coldness of the housing part 110 can prevent overheating of the skin. Therefore, as the skin is cooled, pain caused by heat can be remarkably reduced. Further, damage to or deformation of the housing part 110 caused by heat generated from the ultrasonic wave generator 160 can be prevented. Various types of cooling elements, such as a cooling element circulating a cooling medium to generate cold air or supplying electricity to generate cold air, may be applied as the cooler 170.

The housing part 110 includes a housing body part 120, a housing cover part 130, and a heat conductor 140.

The holder part 150 is accommodated in the housing body part 120. A plurality of fastening hole parts 123 are formed in the housing body part 120. A sealing film part 125 is installed at one side of the housing body part 120 to prevent leakage of the medium and allow passage of ultrasonic waves. The sealing film part 125 may be laminated on a lower side of the housing body part 120.

The housing cover part 130 is coupled to the housing body part 120 and is irradiated with ultrasonic waves generated from the ultrasonic wave generator 160. The contact part 131 is formed at one side of the housing cover part 130 to come in contact with the skin and irradiate the skin with the ultrasonic waves. The contact part 131 may be formed in an annular shape. Also, a plurality of hook parts 133 are formed on the housing cover part 130, and a restrainer 126 is formed on the lower side of the housing body part 120 so that the hook part 133 is caught in and restrained by the restrainer 126.

The heat conductor 140 is connected to the housing body part 120 and the cooler 170 to cool the housing body part 120. A plurality of through-hole parts 145 are formed in the heat conductor 140, and the plurality of fastening hole parts 123 are formed in the housing body part 120 to correspond to the through-hole parts 145. As a fastening member 146 passes through the through-hole part 145 and is fastened to the fastening hole part 123, the heat conductor 140 is coupled to the housing body part 120. Since the heat conductor 140 is connected to the housing body part 120 and the cooler 170, cooling energy of the cooler 170 is conducted to the housing body part 120 and the housing cover part 130 through the heat conductor 140. As the housing body part 120 is cooled by the heat conductor 140, the medium accommodated in the housing body part 120 is cooled. Also, since the contact part 131 of the housing cover part 130 is cooled as the housing body part 120 conducts the cooling energy to the housing cover part 130, as the skin is cooled by the housing cover part 130, pain caused by heat can be remarkably reduced.

The holder part 150 includes a holder body part 151 in which the accommodation space part 121 is formed, a lid part 153 configured to cover an opening of the holder body part 151, and a sealing part 154 interposed between the lid part 153 and the holder body part 151 to seal a gap between the lid part 153 and the holder body part 151. The lid part 153 may be formed in a plate shape to cover the accommodation space part 121, and the sealing part 154 may be formed in the shape of a quadrangular frame along the periphery of the lid part 153. An injection part 155 is formed in the lid part 153 to inject a medium into the accommodation space part 121, and the injection part 155 is closed by a stopper part 156. A plurality of holder fastening parts 152 are formed on the lid part 153, and the plurality of holder fastening parts 152 are each fastened to a groove part 127 of the housing body part 120. Here, the sealing part 154 seals a gap between the housing body part 120 and the lid part 153.

The housing body part 120, the housing cover part 130, and the heat conductor 140 are formed of a thermally conductive material. For example, the housing body part 120, the housing cover part 130, and the heat conductor 140 include an aluminum material. Accordingly, cold air generated from the cooler 170 may be conducted to the housing body part 120 and the housing cover part 130 through the heat conductor 140 to cool the ultrasonic wave generator 160, and the skin can be cooled for skin treatment or skin care. Also, since the cold air of the cooler 170 cools the ultrasonic wave generator 160 through a medium, overheating of the ultrasonic wave generator 160 can be prevented, and the operation time of the ultrasonic wave generator 160 can be significantly increased. Therefore, the use time of the beauty care apparatus 100 can be significantly increased. Further, damage to or deformation of the housing part 110 caused by heat generated from the ultrasonic wave generator 160 can be prevented.

The cooler 170 includes a plurality of Peltier elements disposed in a peripheral direction of the housing part 110 at one side of the housing part 110. The plurality of Peltier elements may be vertically disposed at the one side of the housing part 110. The number of Peltier elements may be appropriately determined in consideration of the capacity of the Peltier element, the capacity of the ultrasonic wave generator 160, the size of the beauty care apparatus 100, and the like.

A plurality of heat conductors 140 installed to surround the housing body part 120. Since the plurality of heat conductors 140 cool the housing body part 120, the housing body part 120 may be thoroughly cooled. Therefore, various heat transfer paths may be configured by the heat conductors 140. The number of installed heat conductors 140 may be appropriately determined in consideration of the capacity of the ultrasonic wave generator 160 or the size of the beauty care apparatus 100.

The heat conductor 140 includes a contact panel part 141 configured to come in contact with the cooler 170 and a heat conduction panel part 142 configured to extend from the contact panel part 141 to come in contact with an outer side surface of the housing body part 120. The contact panel part 141 is vertically disposed to come in close contact with a cooling surface part 171 of the cooler 170, and the contact panel part 141 and the heat conduction panel part 142 are vertically disposed in the longitudinal direction of the housing body part 120. The contact panel part 141 and the heat conduction panel part 142 are each formed in the shape of a vertical plate.

A flat part 122 is formed on the outer side surface of the housing body part 120, and a flat heat conduction surface part 143 is formed on the heat conduction panel part 142 to come in contact with the flat part 122. Accordingly, a thermal contact area of the housing part 110 and the heat conduction panel part 142 may be increased. Also, a plurality of heat conduction fin parts (not illustrated) may be formed on the outer side surface of the housing body part 120, and heat conduction groove parts (127) may be formed in the heat conduction panel part 142 so that the heat conduction fin parts are fitted into the heat conduction groove parts. Forms of contact between the housing body part 120 and the heat conduction panel part 142 may vary.

The beauty care apparatus 100 further includes a heat dissipation unit 180 configured to come in contact with a plurality of heat generation surface parts 172 so that heat is dissipated from the plurality of heat generation surface parts 172. Since the heat dissipation unit 180 comes in contact with the plurality of heat generation surface parts 172, heat may be promptly dissipated from the plurality of heat generation surface parts 172. Therefore, the cooling efficiency of the Peltier elements can be further improved.

The heat dissipation unit 180 includes a heat dissipation block 181, a supply tube part 185, and a discharge tube part 186.

The heat dissipation block 181 is seated on the plurality of heat generation surface parts 172 and has a heat dissipation space part 182 formed therein. The heat dissipation block 181 may be made of an aluminum material or the like with excellent thermal conductivity. A plurality of heat dissipation fins may be formed to protrude from the heat dissipation space part 182 to increase the heat exchange efficiency of a heat dissipation medium. The heat dissipation block 181 is formed in the shape of a quadrangular block to come in close contact with the heat generation surface parts 172 of the Peltier elements.

The supply tube part 185 is connected to the heat dissipation block 181 to supply a heat dissipation medium to the heat dissipation space part 182. The supply tube part 185 is connected to a side of the heat dissipation block 181 that is opposite to the housing part 110. The supply tube part 185 is connected to a cooling tank (not illustrated) of the beauty care apparatus 100. The cooling tank may accommodate the heat dissipation medium and have a radiator or the like installed therein to cool the heat dissipation medium.

The discharge tube part 186 is connected to the heat dissipation block 181 to discharge the heat dissipation medium from the heat dissipation space part 182. The discharge tube part 186 is connected to the side of the heat dissipation block 181 that is opposite to the housing part 110. The discharge tube part 186 is connected to the cooling tank of the beauty care apparatus 100.

The supply tube part 185 supplies the heat dissipation medium to the heat dissipation block 181, and the heat dissipation medium heat-exchanged at the heat dissipation block 181 is discharged to the cooling tank through the discharge tube part 186. Therefore, as hot air of the heat generation surface parts 172 of the Peltier elements is released to the heat dissipation medium through the heat dissipation block 181, overheating of the Peltier elements can be prevented.

The present disclosure has been described above with reference to the embodiments illustrated in the drawings, but the embodiments are only illustrative, and those of ordinary skill in the art should understand that various modifications and other equivalent embodiments are possible from the embodiments described herein. Therefore, the true technical protection scope of the present disclosure should be defined by the claims below.

The invention claimed is:

1. A beauty care apparatus comprising:
   a housing part configured to accommodate a medium therein and formed of a thermally conductive material;
   a holder part disposed inside the housing part, and including a holder body part having a flat part formed on an outer side surface;
   an ultrasonic wave generator configured to be coupled to the holder part and generate ultrasonic waves; and
   a cooler installed in the housing part to cool the housing part,
   wherein the housing part includes:
      a housing body part configured to accommodate the holder part;
      a housing cover part configured to be coupled to the housing body part and configured to be irradiated with ultrasonic waves generated from the ultrasonic wave generator; and
      a heat conductor connected to the housing body part and the cooler to cool the housing body part,
   wherein the heat conductor includes:
      a contact panel part configured to come in contact with the cooler; and
      a heat conduction panel part configured to extend from the contact panel part to come in contact with an outer side surface of the housing body part
   wherein:
      a flat part is formed on the outer side surface of the housing body part; and
      a flat heat conduction surface part is formed on the heat conduction panel part to come in contact with the flat part of the housing body part,
   wherein the cooler is a plurality of Peltier elements disposed in a peripheral direction of the housing part at one side of the housing part,
   further comprising a heat dissipation unit configured to come in contact with a heat generation surface part of each of the plurality of Peltier elements so that heat is dissipated from the heat generation surface part,
   wherein the flat part of the holder body part contacts an inner side surface of the housing body part, and the flat part of the housing body part contacts the flat heat conduction surface part, and
   wherein the heat dissipation unit is interposed between the plurality of Peltier elements, and the plurality of Peltier elements are arranged facing each other.

2. The beauty care apparatus of claim 1, wherein the housing body part, the housing cover part, and the heat conductor are formed of a thermally conductive material.

3. The beauty care apparatus of claim 2, wherein the heat conductor is provided as a plurality of heat conductors installed to surround the housing body part.

4. The beauty care apparatus of claim 1, wherein the heat dissipation unit includes:
   a heat dissipation block configured to come in contact with the plurality of heat generation surface parts and have a heat dissipation space part formed therein;
   a supply tube part connected to the heat dissipation block to supply a heat dissipation medium to the heat dissipation space part; and a discharge tube part connected to the heat dissipation block to discharge the heat dissipation medium from the heat dissipation space part.

5. The beauty care apparatus of claim 4, wherein the plurality of Peltier elements are installed in an upright state on an outer side surface of the heat dissipation block.

\* \* \* \* \*